United States Patent [19]

Hashim

[11] Patent Number: 4,637,054

[45] Date of Patent: Jan. 13, 1987

[54] INSPECTING ARTICLES

[75] Inventor: Abdullah Hashim, Leicester, Fed. Rep. of Germany

[73] Assignee: Kearney & Trecker Marwin Limited, Brighton, England

[21] Appl. No.: 636,498

[22] Filed: Aug. 1, 1984

[30] Foreign Application Priority Data

Nov. 23, 1983 [GB] United Kingdom ............... 8331248

[51] Int. Cl.$^4$ .............................................. G06K 9/20
[52] U.S. Cl. ........................................ 382/8; 382/18
[58] Field of Search .................. 382/8, 18, 51, 9, 22; 356/237; 358/107, 106

[56] References Cited

U.S. PATENT DOCUMENTS

| | | | |
|---|---|---|---|
| 3,662,341 | 5/1972 | Baumgartner et al. | 382/51 |
| 4,071,899 | 1/1978 | Holy | 364/561 |
| 4,075,604 | 2/1978 | Degasperi | 382/18 |
| 4,110,736 | 8/1978 | Kono | 382/22 |
| 4,221,297 | 9/1980 | Lopez et al. | |
| 4,351,437 | 9/1982 | Long | |
| 4,365,304 | 12/1982 | Ruhman et al. | 382/51 |
| 4,377,238 | 3/1983 | Wilks et al. | 358/106 |
| 4,403,294 | 9/1983 | Hamada et al. | 358/106 |
| 4,414,566 | 11/1983 | Peyton et al. | 382/42 |
| 4,493,420 | 1/1985 | Dennis | 382/45 |
| 4,549,205 | 10/1985 | Misaki et al. | 358/106 |

FOREIGN PATENT DOCUMENTS

| | | |
|---|---|---|
| 0052813 | 8/1982 | European Pat. Off. |
| 1298953 | 12/1972 | United Kingdom |
| 1392448 | 4/1975 | United Kingdom |
| 1527600 | 10/1978 | United Kingdom |
| 2009395 | 6/1979 | United Kingdom |
| 2020945 | 11/1979 | United Kingdom |
| 2027538 | 2/1980 | United Kingdom |
| 2031684 | 4/1980 | United Kingdom |
| 2032618 | 5/1980 | United Kingdom |
| 2057124 | 3/1981 | United Kingdom |
| 2087548 | 5/1982 | United Kingdom |
| 2107858 | 5/1983 | United Kingdom |

Primary Examiner—Stephen A. Kreitman
Attorney, Agent, or Firm—Oblon, Fisher, Spivak, McClelland & Maier

[57] ABSTRACT

The condition of an article e.g. a multihead tool array is compared after having been subjected to some operation with its previous condition e.g. before and after a drilling or other operation of the tool array by forming an image, e.g. a video image, of the article before the operation and automatically comparing it with a second such image formed after the operation. Known image enhancement techniques can be used, and statistical techniques used in data processing equipment to detect significant differences between the images.

11 Claims, 4 Drawing Figures

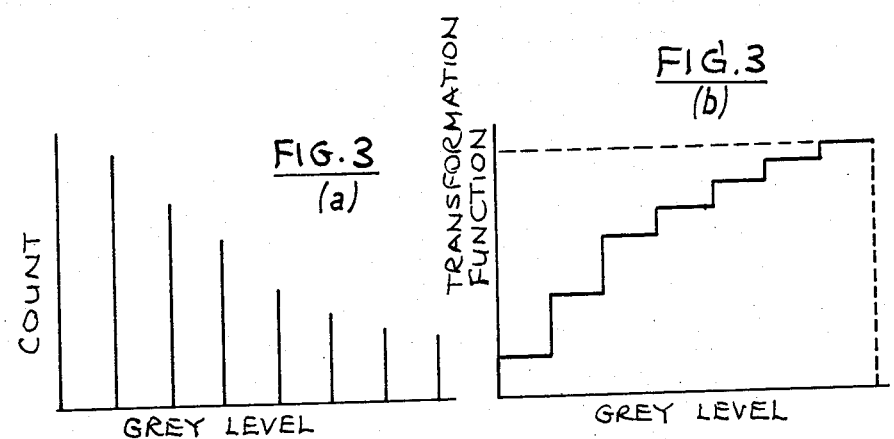
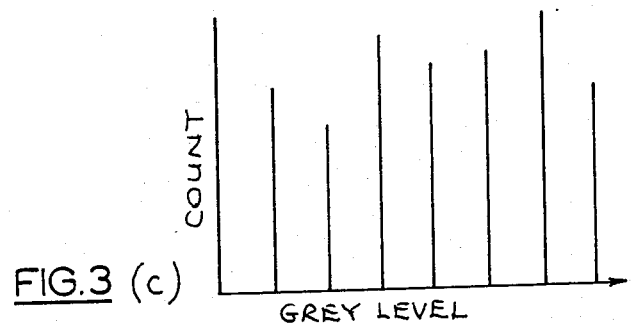
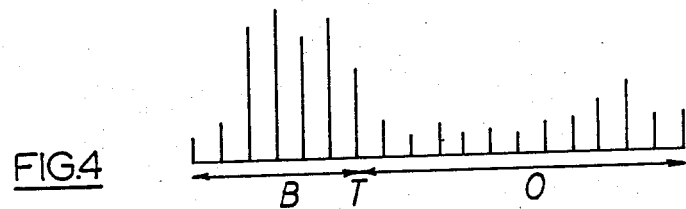

INSPECTING ARTICLES

BACKGROUND OF THE INVENTION

This invention relates to methods and apparatus for comparing the condition of an article at different times.

In many industrial applications, it is important to know that the condition of an article after having been subjected to some operation is unchanged. An example is a drill bit or a multihead tool array where the or a drill or other tool might become damaged during a drilling operation and it is important that the damage be discovered and the machine stopped before proceeding to the next operation. The problem is aggravated by the fact that different tools or tool arrays might be used in succession.

BRIEF DESCRIPTION OF THE INVENTION

The invention provides a solution to this problem.

The invention comprises a method for comparing the condition of an article at different times comprising forming an image of the article at a first time, forming another image of the article at a second time and comparing the two images automatically to detect significant differences.

The images may be formed electronically, and may be video images.

The first image is preferably digitised and processed in various ways both to enhance it and to identify areas of interest. Image enhancement is effected by any one or more of a variety of known techniques. For example, improved signal-to-noise ratio is achievable by combining information from multiple frames of a video image. A digitised video image may be enhanced by histogram modification techniques, image smoothing may be achieved by filtering out low frequency noise, and the image may be sharpened by known image sharpening algorithms.

Image segmentation, to identify areas of interest, may be effected by point-dependent or region-dependent techniques.

Edges or areas of interest may be detected in a video image by a suitable algorithm and weights may be assigned to individual pixels of the image according to the probability of their representing areas of interest. In this way, a database is formed from the first image which is then used to compute the probability that the second image is not significantly different from the first image.

In practice, a multiple tool array will be imaged by a video camera and all or as many as required of the operations above referred to will be effected on the image. During this time, the multiple tool array will be used to perform whatever function is required on a workpiece. Then the multiple tool array is returned to the position in which it was first imaged and a second video image made. This is compared to the first image using the database evaluated during the time the tool array was performing its operation. This comparison can be carried out very rapidly, and, if no significant change is detected, the machine stepped on to its next operation. This may, of course, be a repetition of the first operation, or, more usually, it will be a different operation using a different tool array. If a significant change is detected between the before-and-after images, the machine may be stopped and an alarm raised or an automatic tool changing operation effected.

BRIEF DESCRIPTION OF THE DRAWINGS

Embodiments of methods and apparatus for comparing the condition of articles at different times according to the invention will now be described with reference to the accompanying drawings, in which:

FIG. 3(a) is a histogram of grey levels in an image,

FIG. 3(b) is a graph of a transformation function, and

FIG. 3(c) is an equalized histogram made by operation on the histogram of FIG. 3(a) with the transformation function of FIG. 3(b), and FIG. 4 is a diagram illustrating grey-level segmentation by histogram thresholding.

DETAILED DESCRIPTION OF THE PREFERRED EMBODIMENTS

Figure 1:
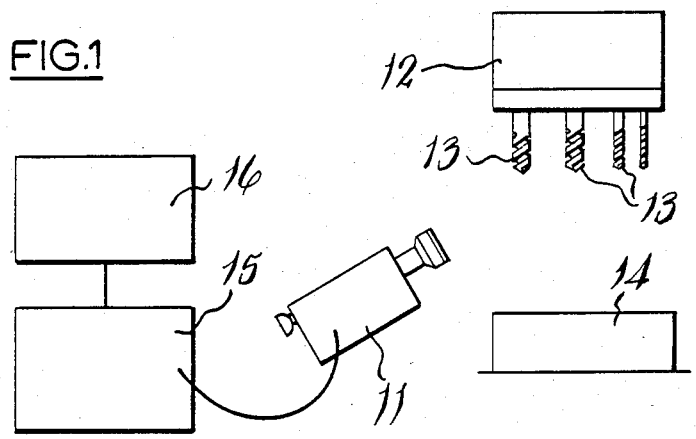
FIG. 1 is a diagrammatic illustration of a system for detecting broken tools in multiple tool arrays.

The system illustrated in FIG. 1 comprises a video camera 11 aimed at a multiple tool head 12 having a plurality of different drill bits and taps 13 when the head is in an inspection position just prior to performing an operation on a workpiece 14.

The tool head 12 is one of several such heads, all different, which are required to perform successive operations on the workpiece.

The camera 11 is so positioned that no one of the tools obscures another from the camera's view. More than one camera can be used, of course, where a single camera cannot be so positioned.

Figure 2:
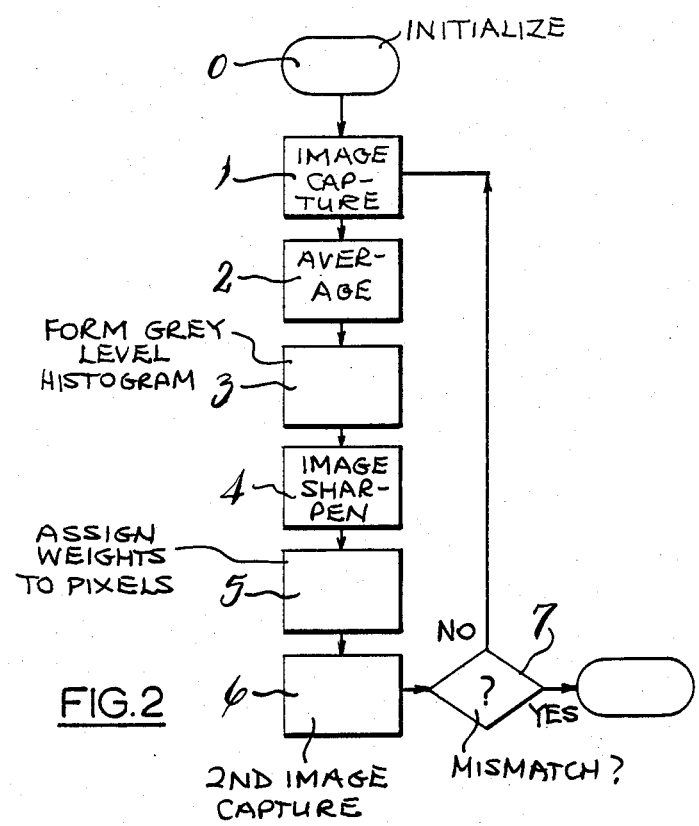
FIG. 2 is a flow chart showing the operation of the system illustrated in FIG. 1.

The procedure is illustrated by the flow diagram of FIG. 2. At step 0, the arrangement is initialized by selecting appropriate operating modes for the equipment—this of course may be built-in as a single operational mode or preset as system defaults so that initialization is effected simply by switching the system on.

Eight image frames formed by the video camera 11 are captured at step 1 and averaged in a real time data capture arrangement 15, in which the grey levels of the individual pixels of the image are stored in RAM locations that map on to the image. The eight frames are averaged at step 2 to improve signal to noise level. The resolution of the system will be selected according to the requirements of the application—looking at a large area containing a number of fine tools will clearly require better resolution than looking at a small area containing relatively large tools. It may be provided that different resolutions can be defined in the same system ranging from an image size of 1024×512 at the highest resolution to a size of 256×256 at the low resolution end.

The signal to noise improved image resulting from the averaging process is then further processed in a computer 16.

Step 3, carried out in the computer, involves forming a histogram of the grey levels in the image. The histogram is then equalized by operating on the grey level frequencies with a transformation function so as to obtain an equalized histogram with a more uniform distribution of grey levels. FIG. 3 shows (graph (a)) an original histogram, a transformation function (graph (b)) and the equalized histogram (graph (c)). From the equalized histogram is formed a new histogram with two distinct grey level regions, one corresponding to the grey levels of tools and one corresponding to the grey level of the background. This facilitates discrimination between tool and background regions of the image. FIG. 4 shows such a processed histogram and illustrated further the technique of histogram thresholding in which the histogram, typical of an image of grey objects against a dark background, is divided by a threshold grey level T into objects levels O and background levels B.

A new digital image, in which the grey levels of the individual pixels have been modified by the transformation function aforementioned and whatever algorithm was used to operate on the equalized histogram, is then scanned to ascertain the positions of edges, which is to say positions in the image where the grey level changes from O to B. A new image is created at this stage in which only two grey levels $L_O$ and $L_B$ are present, by redefining the grey level of each pixel to be $L_O$ or $L_B$ according as the pixel belongs to the range O of object levels or the range B of background levels.

The grey level segmented image is sharpened by differentiation techniques to detect edges and so, at step 4, to identify those pixels of the image belonging to the tools 13.

At step 5, a statistical measure is computed which assigns weights to pixels according as the pixels are on the edges of the tools or inside the tools, and according as the tools are large or small. Pixels in large tools are given a low weight, since it is assumed that large tools will break relatively infrequently as compared to small tools. Pixels on the edges of tools are given a low weight since a difference detected between the "before" and "after" images might signify only that the tool is differently orientated or that it has picked up some swarf. The object of this last processing step on the "before" image is to reduce the amount of data that has to be dealt with at the comparison stage.

The next step in the operation, then, is to capture the image after the tool head 12 has performed its operation in the workpiece 14. The tool head 12 is for this returned to the inspection position. The image thus captured is checked against the data from step 5 at step 7. If there is no mismatch, it is assumed that no tool has broken, and the process returns to step 1 ready for the next operation. Otherwise it is assumed breakage occurred, and the machinery may be stopped and/or an alarm raised.

The next operation might use the same tool head or it might use a different tool head. In either event a new image is made at step 1.

The image processing techniques outlined above could of course be replaced or supplemented by other techniques known in the art of image processing.

The invention is not of course limited to the inspection of tools or arrays of tools. Essentially, any object or succession of objects which might be similar or different can be inspected at different times to detect significant changes, the determination of what is significant being built in to the image processing technique by assigning appropriate weights to the pixels of interest in the ordinarily captured image.

The invention enables inspection to take place automatically and very rapidly. The bulk of the image processing is effected while the article being inspected is doing whatever it is that gives rise to the need for an "after" inspection—drilling, for example, in the case of drills. Capture of the "after" image and the comparison with the reduced data set is effected extremely rapidly using modern computer techniques, and this is of course important in such operations as automated drilling and tapping of workpieces in that no undue delay is introduced between one operation and the next.

What I claim is:

1. A method for comparing the condition of an article at different times before and after subjecting the article to some operation, comprising the steps of
   (a) forming a first image of the article before the said operation,
   (b) storing said first image,
   (c) forming a second image of the article after the said operation,
   (d) predetermining what differences between said first and second images would be significant if detected, and
   (e) comparing said stored first and said second images automatically to detect such significant differences.

2. A method for repeatedly comparing the condition of an article at different times before and after subjecting the article to each operation of a succession of operations, comprising the steps of
   (a) forming a first image of the article before each said operation,
   (b) storing said first image,
   (c) forming a second image of the article after each said operation,
   (d) predetermining what differences between said first and second images would be significant if detected, and
   (d) comparing said stored first and said second images automatically to detect such significant differences.

3. A method for comparing the condition of a succession of articles at different times before and after subjecting said articles to operations, comprising the steps of
   (a) forming a first image of each article before subjecting it to its said operation,
   (b) storing said first image,
   (c) forming a second image of each article after subjecting it to its said operation,
   (d) predetermining for each article what differences between said first and said second images would be significant if detected, and
   (e) comparing said stored first and said second images automatically to detect such significant differences.

4. A method for comparing the condition of a tool at different times before and after performing an operation on a workpiece, comprising the steps of
   (a) forming a first image of said tool before said operation,
   (b) storing said first image,
   (c) forming a second image of said tool after said operation,
   (d) predetermining what differences between said first and second images would be significant if detected to indicate that the tool is damaged, and
   (e) comparing said stored first and said second images automatically to detect such significant differences.

5. A method for comparing the condition of tools on a multihead tool array at different times before and after performing operations of a workpiece, comprising the steps of
   (a) forming a first image of the tools on each head of said tool array before the operation of said tools,
   (b) storing said first image,
   (c) forming a second image of the said tools after said operation thereof,
   (d) predetermining what differences between said first and second images would be significant if detected to indicate that any tool is damaged during said operation, and
(e) comparing said stored first and said second images automatically to detect such significant differences.

6. A method according to any of claims 1 to 5, in which said first and second images are video images comprised of pixels, the first image at least being digitised and enhanced, further comprising the steps of
(a) detecting by a suitable algorithm areas of interest such as edges and assigning weights to pixels thereby,
(b) forming a database from the said first image which is representative of such areas of interest, and
(c) computing from said database the probability that said second image is not significantly different from said first image.

7. Apparatus for comparing the condition of an article at different times before and after subjecting the article to some operation, comprising
(a) imaging means adapted to form first and second images of said article, before and after said operation respectively,
(b) image store means adapted to receive and store said first image from said imaging means,
(c) difference significance determining means adapted to predetermine what differences between said first and second images would be significant if detected, and
(d) comparator means adapted to compare said stored first and said second images automatically to detect such significant differences.

8. Apparatus for comparing the condition of a tool at different times before and after performing an operation on a workpiece, comprising (a) imaging means adapted to form first and second images of said tool before and after said operations respectively,
(b) image store means adapted to receive and store said first image from said imaging means,
(c) difference significance determining means adapted to predetermine what differences between said first and second images would be significant if detected to indicate that the tool is damaged, and
(d) comparator means adapted to compare said stored first and said second images automatically to detect such significant differences.

9. Apparatus according to claim 8, in combination with a tool head, said imaging means being located at an inspection position for a tool in said head to which position said head is brought before and after said operation.

10. Apparatus according to claim 9, in which said comparator means comprise data processing means adapted to detect edges or areas of interest in a video image and programmed to assign weights to pixels of such image according to an assigned probability of their representing areas of interest and forming a database from the said first image which is representative of preselected areas of interest in the article imaged, and computing means programmed to compute from said database and from said second image the probability that the second image is not significantly different from the first image.

11. Apparatus according to claim 9, said data processing means being adapted to form said database in such short time as it takes the tool head to return to said inspection position after said operation.

* * * * *